United States Patent
Zobele et al.

(10) Patent No.: US 6,775,470 B2
(45) Date of Patent: Aug. 10, 2004

(54) DEVICE FOR THE DIFFUSION OF SOLUTIONS

(75) Inventors: Franco Zobele, Trento (IT); Fabio Marchetti, Povo (IT)

(73) Assignee: Zoeble Holding SpA, Trento (IT)

( * ) Notice: Subject to any disclaimer, the term of this patent is extended or adjusted under 35 U.S.C. 154(b) by 0 days.

(21) Appl. No.: 10/271,812

(22) Filed: Oct. 16, 2002

(65) Prior Publication Data

US 2004/0076410 A1 Apr. 22, 2004

(51) Int. Cl.[7] .............................................. A61M 16/00
(52) U.S. Cl. ..................................... 392/390; 392/395
(58) Field of Search ............................... 392/386, 390, 392/392, 394, 395; 239/34, 44, 135, 136

(56) References Cited

U.S. PATENT DOCUMENTS

| | | | |
|---|---|---|---|
| 5,220,636 A | * | 6/1993 | Chang ......................... 392/392 |
| 5,903,710 A | * | 5/1999 | Wefler et al. ................ 392/392 |
| 5,945,094 A | * | 8/1999 | Martin et al. .............. 424/76.1 |
| 6,145,241 A | * | 11/2000 | Okuno ......................... 43/129 |

FOREIGN PATENT DOCUMENTS

| | | | |
|---|---|---|---|
| DE | 41 31 613 | | 3/1993 |
| DE | 4446413 | * | 6/1996 |
| EP | 0 722 742 | | 7/1996 |
| EP | 0 943 344 | | 9/1999 |
| EP | 0 945 062 | | 9/1999 |
| WO | WO98/46283 | | 10/1998 |
| WO | WO98/46285 | | 10/1998 |

* cited by examiner

Primary Examiner—Sang Y Paik
(74) Attorney, Agent, or Firm—Merchant & Gould

(57) ABSTRACT

A device (1) for the diffusion of solutions is made up of a heating device (50) comprising a shell, formed by two half-shells (51, 52), inside which there is an electric resistance (R1), designed to heat up when an electric current is applied to it, and a refill (1) comprising a shell (4, 5) containing the solution to be diffused and a wick (3) soaked in said solution and comprising at least one part that is in contact with the outside to diffuse the said solution. The refill (1) is coupled to the heating device (50) so that the resistance (R1) may heat the wick (3) causing the evaporation of the solution. The shell (5) of the refill (1) is provided with engaging devices (19) that will fit into the complementary engaging devices (55) provided in the shell (51) of the heating device (50), so that the refill (1) may be coupled with the heating device and may be turned on it so that it may be positioned in such a way as to prevent leakage of the solution it contains, whatever the direction in which the power socket on the wall is installed.

15 Claims, 3 Drawing Sheets

DEVICE FOR THE DIFFUSION OF SOLUTIONS

DESCRIPTION

This invention refers to a device for the diffusion of solutions, in particular to a heating device that may be attached to a refill fitted with an evaporation wick used to diffuse solutions containing active principles such as deodorants, insecticides, disinfectants and similar substances.

Several kinds of diffuser devices are currently sold on the market, comprising electric heating devices provided with an electric plug to be inserted into a power socket thereby powering an electric resistance which then heats up. These heating devices are coupled to a refill containing a solution and fitted with an evaporation wick which, when heated by contact with the resistance, diffuses the solution.

Diffuser devices according to the prior art have drawbacks.

Such diffuser devices are rather complex, bulky and costly, above all due to the refill structure, which generally includes a bottle with a related undercap and cap to connect it to the wick and to the heating device.

A further drawback of known diffuser devices is the fact that the refill is rigidly fixed to the heating device. As a consequence, depending upon the positioning (vertical, horizontal or oblique) of the power socket into which the plug of the device is inserted, the refill may be placed incorrectly causing spillage of the solution it contains.

An aim of this invention is to eliminate such drawbacks in the known art, providing a solution diffusing device which is both economical and simple to manufacture.

A further aim of this invention is to provide such a solution diffusing device made up of a limited number of components, with a simplified structure that is easy to assemble.

A further aim of this invention is also to provide a solution diffusing device that is compact, practical, versatile and suitable to be inserted into power sockets which have been installed in any direction.

These aims have been achieved in accordance with the invention with the characteristics listed in the appended independent claim 1.

Advantageous embodiments of the invention are said in the dependent claims.

The solution diffusing device, according to the invention, comprises a heating device comprising a shell inside which there is an electric resistance which heats up, when an electric current is applied to it, and a refill comprising a shell containing the solution to be diffused and a wick soaked in the solution. The wick provides at least a part communicating with the outside of the refill to diffuse the solution. The refill is attached to the heating device in such a way that the resistance may heat the wick and cause the evaporation of the solution.

The peculiar characteristic of the invention is the fact that the refill shell comprise some engagement means which can be engaged with corresponding engagement means provided in the heating device shell, so that the refill may be coupled to the heating device and turned with respect to it, so that it can be arranged in a position that avoids any spillage of the solution the refill contains.

This diffusing device is extremely practical and versatile, since the refill may be turned with respect to the heating device, in a way depending from the direction in which the power socket where the heating device is inserted has been installed. Additionally, the refill may be made, separately from the heating device, in a simple and economic structure.

Further characteristics of the invention will appear clearer from the following detailed description, referring to a purely exemplary and therefore non-limiting embodiment thereof, illustrated in the appended drawings, in which.

Figure 1:
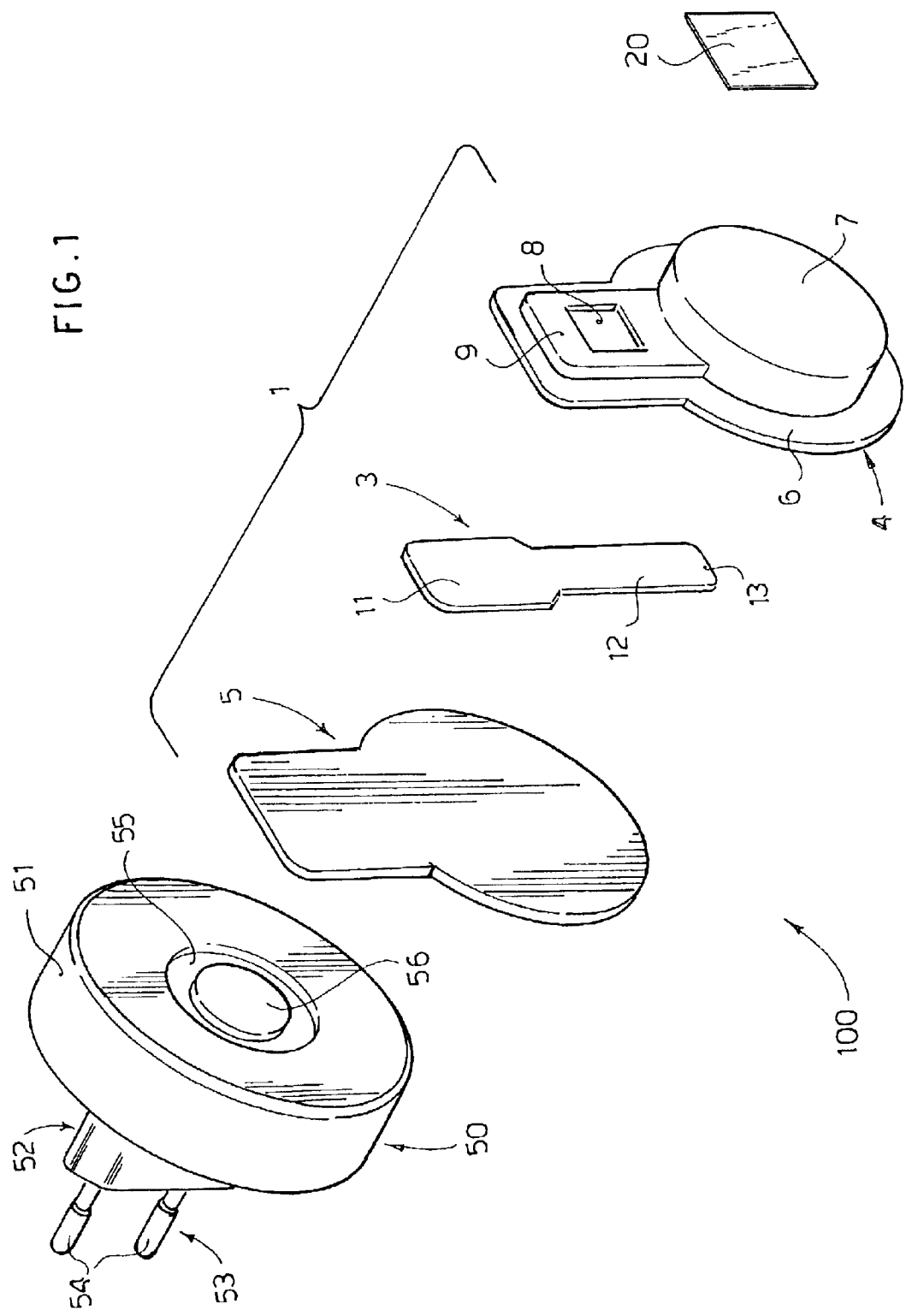
FIG. 1 is a perspective, exploded view of the solution diffusing device according to the invention.

The solution diffusing device, indicated as a whole with reference number 100, is described with the aid of the Figures.

Diffusing device 100 comprises a heating device 50 and a refill 1.

Refill 1 comprises a shell or valve to contain the solution and a wick 3 used to diffuse the solution.

The shell consists of a front half-shell or half-valve 4 designed to contain the solution and a rear half-shell or half-valve 5 which serves as a cover and may be coupled to front half-shell 4.

Front half-shell 4 has a flat peripheral flange 6 which surrounds a recessed chamber or reservoir 7 to contain the solution. Next to chamber 7 is a recess 9 with a substantially rectangular opening 8.

In the wall of chamber 7 opposite the wall separating it from opening 8 there is a slot 10 to hold wick 3 in position.

Wick 3 is in the shape of an essentially rectangular plate with a wider head part 11 and a narrower stem 12. Head part 11 of wick 3 is designed to fit into recess 9 in the front half-shell 4. Holes may be provided in head part 11 of the wick to improve the evaporation of the solution.

The outside surface of recess 9 has a peelable band 20 which covers opening 8. Band 9 may be an adhesive strip and may be pulled by the user to uncover opening 8.

Stem 12 of wick 3 is sufficiently long to span the whole width of chamber 7 in the front half-shell 4. Stem 12 has a free end 13 designed to fit into slot 10 in the front half-shell.

Figure 2:
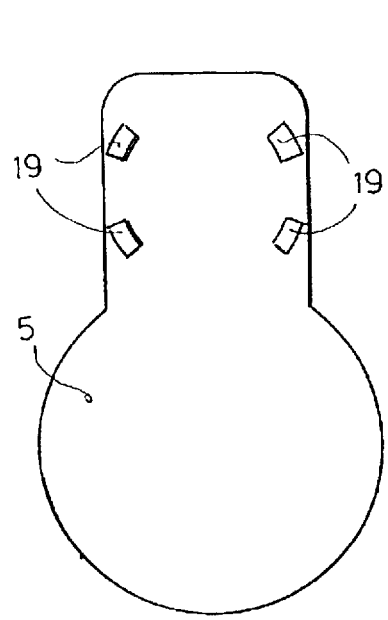
FIG. 2 is an elevational rear view of the refill for the diffuser device in FIG. 1.
Figure 3:
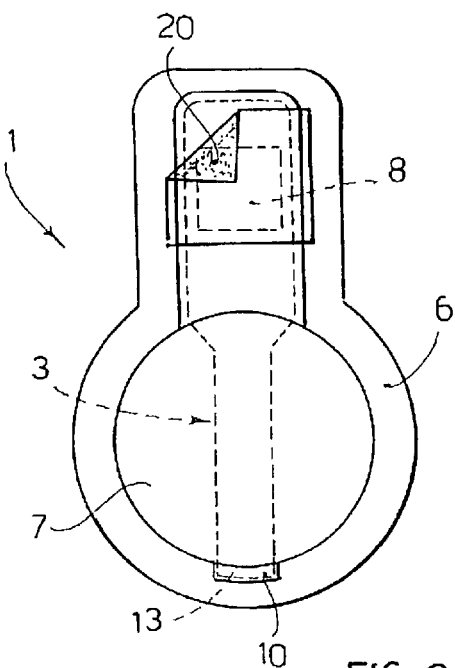
FIG. 3 shows a front elevational view of the diffuser device in FIG. 1.

Rear half-shell or cover 5 is shaped like a flat plate with the same outer profile as front half-shell 4. As shown in FIG. 2, on the inside surface of rear half-shell 5 a number of projections or teeth 19 are placed in an annular arrangement. Teeth 19 should preferably be four in number, placed in pairs positioned diametrically opposite one another.

Heating device 50 comprises a front half-shell 51 and a rear half-shell 52 which fit together. The two half-shells 51 and 52 may be fitted together using suitable mechanical means, such as clips or interlocking devices or may be joined together by hot welding or ultrasonic welding. Rear half-shell 52 incorporates an electric plug 53.

Merely as an example, the electric plug illustrated in the drawings shows a standard two-pin Italian plug, with two electric poles 54, suitable for insertion into power sockets with two or three holes to accept poles 54. However, any other type of plug may be fitted to rear half-shell 52 of heating device 51, such as for example three-pin plugs with poles of various gauges, or standard American plugs.

Front half-shell 51 of heating device 50 is substantially shaped like a circular plate and has a circular or annular channel 55 in its outside face which has a radius substantially matching the radius of the circular positioning of projections 19.

Annular or circular channel 55 is substantially as wide as the thickness of projections 19, so that projections 19 fit into circular channel 55, permitting the rotation of refill 1 on heating device 50 along the circular path defined by circular channel 55.

Figure 4:
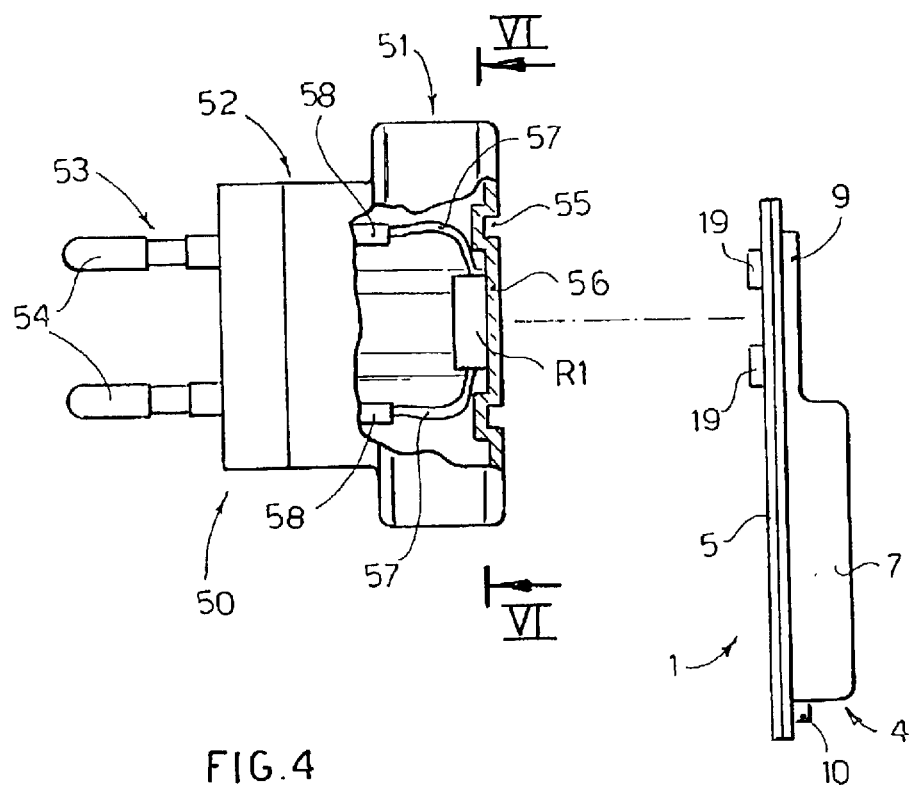
FIG. 4 is a exploded side view of a refill and a heating device, the heating device is shown in part-sectional view with the plug placed in a vertical position.
Figure 5:
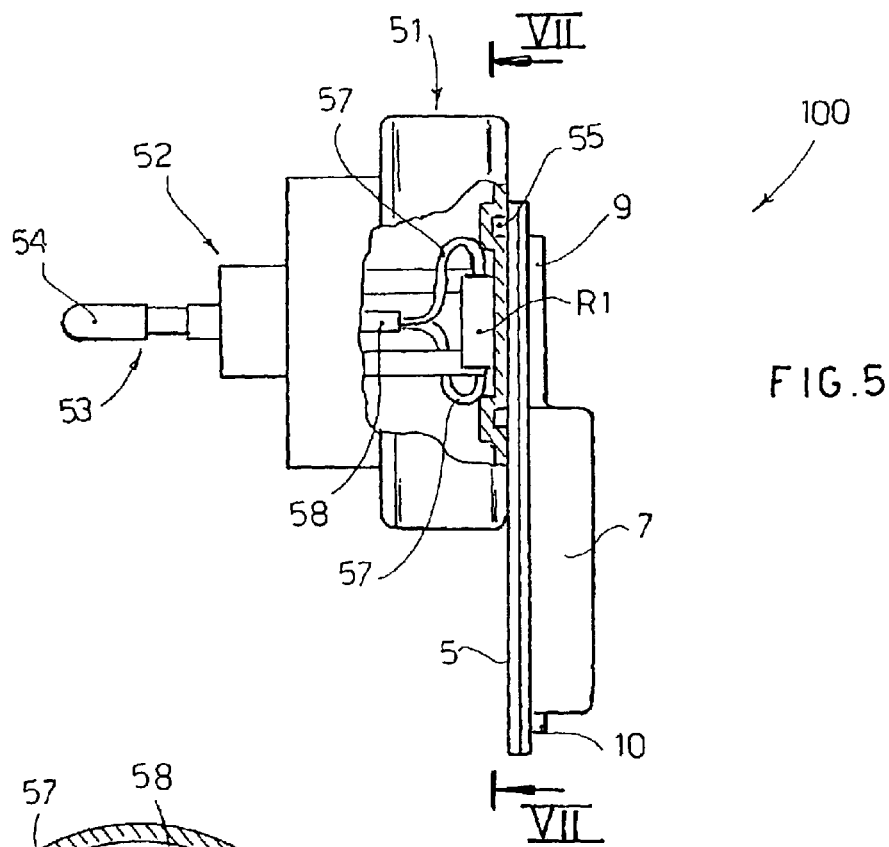
FIG. 5 is a side view, similar to FIG. 4, showing the refill assembled to the heating device, in which the heating device is shown in part-sectional view and placed with the plug in a horizontal position.

Annular channel 55 delimits a disc-shaped wall 56, behind which an electric resistance R1 is fitted (FIGS. 4 and 5). Electric resistance R1 is connected at its two ends by two respective electric wires 57, to electric contacts 58 connected to the electric poles 54 of plug 53.

Figure 6:
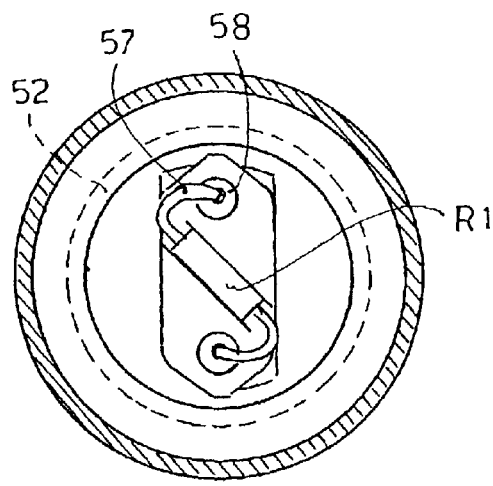
FIG. 6 is a cross-sectional view of the heating device, taken along section plane VI—VI of FIG. 4, showing the arrangement of the resistance, when the heating device plug is placed in a vertical position.
Figure 7:
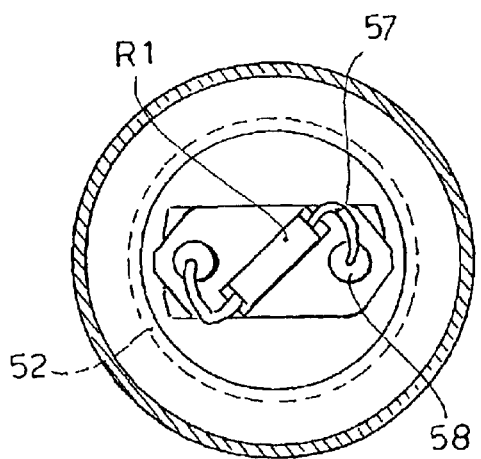
FIG. 7 is view similar to FIG. 6, taken along sectional plane VII—VII of FIG. 5, showing the arrangement of the resistance, when the heating device plug is placed in a horizontal position.

Resistance R1 is fitted on the inside surface of wall 56 of heating device 50, and the axis of resistance R1 is positioned at an oblique angle of approximately 45° in relation to the plane upon which the two poles 54 of plug 53 are placed. In this way, both when the plane of the two poles 54 is positioned vertically (FIG. 6) and when the plane of the two poles is positioned horizontally (FIG. 7), resistance R1 is always positioned at an oblique angle of approximately 45° in relation to a vertical line and a horizontal line, thereby producing substantially the same heating effect on refill 1.

Assembly of diffusing device 100 is extremely simple. In fact, after filling chamber 7 with a liquid solution, upper part 11 of wick 3 must be fitted into recess 9 of the front half-shell 4 and free end 13 of stem 12 of the wick must be inserted into slot 10 of front half-shell 4, in such a way that stem 12 becomes soaked in the liquid in chamber 7.

The rear half-shell 5 must then be coupled to the front half-shell 4 in order to hermetically seal chamber 7 and maintain wick 3 sandwiched between the two half-shells 4 and 5.

Refill 1 is subsequently connected to heating device 50 inserting projections 19 of the rear half-shell of the refill into circular channel 55 of the front half-shell of the heating device. In this way, refill 1 is connected to the heating device and may be turned along the circular path of circular channel 55. This permits the refill to be turned so that solution reservoir chamber 7 may be positioned at the bottom and upper part 11 of wick 3 at the top, thus avoiding any spillage of the solution.

Once refill 1 has been assembled, opening 8 of front half-shell 4 is covered with peelable strip 20 so as to guarantee that the refill does not leak before use and also permit subsequent closure of the refill, should it be necessary to transport the device elsewhere or interrupt its operation.

When plug 53 is inserted into a power socket, the current powers resistance R1 which heats up exchanging its heat with wall 56 and rear half-shell 5 of the heating device and with head part 11 of wick 3 by conduction. As a result, head part 11 of the wick heats up too and permits the evaporation of the liquid with which the wick is saturated. Since resistance R1 is always positioned at an angle of approximately 45° to the area of the refill to be heated, no matter how the plug is positioned (FIGS. 6 and 7), the same heating effect will always be determined.

Wick 3 must be made in a suitable material that has the capillarity and porosity characteristics required to transport the liquid contained in chamber 7 from stem 12 towards head part 11 and thus permit evaporation of the liquid from head part 11. For this purpose, the wick may be made in a mixture of cellulose fibre and cotton or may be made in another porous material of any kind such as ceramic, polyethylene fibre, polypropylene fibre, PET (Polyethylene terephthalate) or similar material.

The two half-shells 4 and 5 may be made in any material compatible with the liquid solution to be contained. Nevertheless, it is preferable that the two half-shells 4 and 5 should be made in plastic material. In this case, front half-shell 4 is made by thermoforming to shape chamber 7 and recess 9, and opening 8 is made by die cutting.

Rear half-shell 5 must be made in material that will resist the heat produced by resistance R1. Preferably, the two half-shells 4 and 5 should be made in the same material so that they may be welded to one another. Rear half-shell 5 may be made by moulding so that projections 19 will be more solid and therefore will fit more firmly into circular channel 55 of the heating device.

If weldable plastic material is used, rear half-shell 5 may be welded to front half-shell 4 along peripheral flange 6. Wick 3, at least around the perimeter of its upper part 11 is welded to the two half-shells 4 and 5 to prevent the liquid contained in chamber 7 from leaking out when refill 1 is not in a vertical position. Therefore to ensure that the refill is tightly sealed, the two half-shells 4 and 5 are welded together along their peripheral edge and around the evaporation area in which head part 11 of wick 3 comes into contact with the air.

The material of the two half-shells 4 and 5 must be such that it permits the two half-shells to be welded together and the two half-shells to be welded to the wick. For this purpose, PVC (polyvinyl chloride) treated with polythene may be used or another material that is compatible with the liquid contained in the reservoir which may be coated with glue that reacts with heat thereby welding with both the half-shells 4 and 5 and the wick 3. For example, the two half-shells 4 and 5 and the wick 3 may be made in the same material. A material produced in thermoformed sheets or injection moulded may be used for the two half-shells 4 and 5 and the same material in porous form may be used for wick 3. In this way, wick 3 and the two half-shells 4 and 5 may be welded together by heat sealing, ultrasonic or high-frequency welding. In this way a tight seal is ensured between wick 3 and half-shells 4 and 5 so that the liquid will not leak out. Additionally, since the wick is welded to the half-shells, it is kept rigidly in position and no folds can form during use which would have a negative effect on the evaporation of the liquid.

Numerous variations and modifications of detail within the reach of a person skilled in the art may be made to this embodiment of the invention without departing from the scope of the invention expressed by the appended claims.

What is claimed is:

1. A device for the diffusion of solutions, including:
   a heating device comprising a heater shell inside which there is an electric resistance designed to heat up when an electric current is applied to the resistance, and a refill comprising a refill shell containing the solution to be diffused and a wick soaked with the said solution and comprising at least one part in communication with the outside to diffuse the said solution, said refill being coupled to the said heating device so that the said resistance is operative to heat the said wick causing evaporation of the solution, the refill shell of said refill providing engagement means operative to engage with corresponding engagement means provided in the heater shell of said heating device, so that the said refill is selectably coupled to said heating device in position with respect to said heating device so that said refill is placed in the correct position for use and to prevent leakage of the solution said refill contains.

2. The device of claim 1, wherein said heater shell of the heating device comprises two half-shells fitted together by fixing means.

3. The device of claim 2, wherein said fixing means are clamps, heat sealing or ultrasonic welding.

4. The device of claim 1, wherein said engagement means provided on said refill includes at least one projection and said corresponding engagement means provided in said heating device is a circular channel designed to accept at least one said projection, or vice versa.

5. The device of claim 4, wherein said engagement means of the refill includes four projections arranged in a ring substantially similar to a circular or annular path defined by the circular channel of the heating device.

6. The device of claim 1, wherein said refill shell comprises a front half-shell and a rear half-shell on the outer surface of which the said engagement means of the shell is provided, and said heating device comprises a rear half-shell in which an electric plug is incorporated and connected to said resistance and a front half-shell in which said corresponding engagement means in the heater shell is provided.

7. The device of claim 4, wherein said refill shell comprises a front half-shell and a rear half-shell on the outer surface of which the said engagement means is provided, and said heating device comprises a rear half-shell in which an electric plug is incorporated and connected to said resistance and a front half-shell in which said corresponding engagement means in the heater shell is provided.

8. The device of claim 4, wherein said circular channel delimits a disc-shaped wall of said front half-shell of the heating device on the inside surface of which said resistance is positioned.

9. The device of claim 7, wherein said circular channel delimits a disc-shaped wall of said front half-shell of the heating device on the inside surface of which said resistance is positioned.

10. The device of claim 8, wherein said resistance has an axis positioned at an oblique angle of about 45° to the plane on which poles of a plug are placed.

11. The device of claim 6, wherein said front half-shell of the refill shell has a flat peripheral flange within which a recessed chamber to contain the solution and a recess to house the head part of said wick are defined, and said rear half-shell of the refill shell is in the shape of a flat plate and has substantially the same peripheral profile as said front half-shell of the refill shell so that the rear half-shell of the refill shell is attachable to the peripheral flange of said front half-shell of the refill shell.

12. The device of claim 11, wherein said wick comprises a stem part designed to be immerged in said solution inside said chamber and a head part wider than the stem part and designed to be at least partially in contact with the outside to permit evaporation of the solution.

13. The device of claim 12, wherein said recess to house the head part of said wick is substantially rectangular in shape and is provided with at least one opening to permit the head part of the wick to at least partially communicate with the outside.

14. The device of claim 13, wherein said opening in the front half-shell of the refill shell is closed by a strip which is removable by the user.

15. The device of claim 6, wherein said rear half-shell of said refill shell is made by moulding, so that said engagement means comprises projections solid enough to ensure that the projection fit firmly into a circular channel comprising said corresponding engagement means on the heating device.

* * * * *

UNITED STATES PATENT AND TRADEMARK OFFICE
CERTIFICATE OF CORRECTION

PATENT NO. : 6,775,470 B2
DATED : August 10, 2004
INVENTOR(S) : Zobele et al.

It is certified that error appears in the above-identified patent and that said Letters Patent is hereby corrected as shown below:

<u>Title page,</u>
Item [73], Assignee, "Zoeble" should read -- Zobele --.

Signed and Sealed this

Fourth Day of April, 2006

JON W. DUDAS
*Director of the United States Patent and Trademark Office*